United States Patent [19]

Adams et al.

[11] 4,211,015
[45] Jul. 8, 1980

[54] METHOD AND APPARATUS FOR MAKING NOVEL PARTICULATE COMPOSITIONS

[75] Inventors: Thomas H. Adams, Mission Viejo; James P. Beck, Garden Grove; Robert C. Menson, Newport Beach, all of Calif.

[73] Assignee: Baxter Travenol Laboratories, Inc., Deerfield, Ill.

[21] Appl. No.: 870,537

[22] Filed: Jan. 18, 1978

[51] Int. Cl.³ .............................................. F26B 5/06
[52] U.S. Cl. ............................................. 34/5; 62/57; 62/64; 264/14
[58] Field of Search ................ 34/5; 264/14; 424/177; 62/57, 64, 78

[56] References Cited

U.S. PATENT DOCUMENTS

| | | | |
|---|---|---|---|
| 2,085,391 | 6/1937 | Reichel . | |
| 2,701,703 | 2/1955 | Evers . | |
| 2,751,762 | 6/1956 | Colton . | |
| 2,875,588 | 3/1958 | Berger . | |
| 3,092,553 | 6/1963 | Fisher, Jr. et al. . | |
| 3,092,553 | 6/1963 | Fisher, Jr. et al. | 424/14 |
| 3,162,019 | 12/1964 | Porter et al. . | |
| 3,228,838 | 1/1966 | Rinfret et al. | 264/14 X |
| 3,422,167 | 1/1969 | Bowman et al. | 34/5 |
| 3,449,885 | 6/1969 | Starkey, Jr. . | |
| 3,484,946 | 12/1969 | Sawer | 34/5 |
| 3,498,069 | 3/1970 | Waldin . | |
| 3,653,222 | 4/1972 | Dunn et al. . | |
| 3,655,838 | 4/1972 | Price et al. . | |
| 3,721,725 | 3/1973 | Briggs et al. | 264/6 |
| 3,857,974 | 12/1974 | Aref et al. | 62/64 |
| 3,928,566 | 12/1975 | Briggs et al. | 424/94 |
| 3,932,943 | 1/1976 | Briggs et al. | 34/5 |

FOREIGN PATENT DOCUMENTS 314639 7/1929 United Kingdom .

OTHER PUBLICATIONS

Heckly, "Cryobiology" 2(3):139–142 (1965).
Maister et al., "Ind. Eng. Chem." 50:623–626, (1958).
Meryman et al., "Proc. Soc. Exp. Biol. Med." 8:587–589 (1960).
Briggs, Manuscript of a Presentation Prepared for the International Symposium on "Freeze Drying" of Biological Products, Oct. 10–13, 1976, Washington, D.C.
Anderson et al., "The Joint National Institutes of Health"-Atomic Energy Commission Zonal Centrifuge Development Program Semiannual Report for Period Jul. 1–Dec. 31, 1962, pp. 60–68.

*Primary Examiner*—John J. Camby
*Attorney, Agent, or Firm*—Paul C. Flattery; Lawrence W. Flynn; Max D. Hensley

[57] ABSTRACT

An improved method and apparatus is disclosed for producing frozen particulate compositions from liquid feedstock. A continuous stream of liquid feedstock is passed through an orifice and into a liquid freezant without the orifice contacting the freezant. Compositions produced by this improved method have low proportions of fine and large particles, yielding particularly beneficial results in the case of quality control materials. The compositions are advantageously employed in automated weighing and filling apparatus.

25 Claims, 2 Drawing Figures

METHOD AND APPARATUS FOR MAKING NOVEL PARTICULATE COMPOSITIONS

This invention broadly relates to methods for preparing lyophilized particles from liquid feedstocks. More specifically, this invention relates to processes and apparatus for manufacturing frozen pellets or particles from such feedstocks, including processes and apparatus for disintegrating liquid feedstocks into discrete droplets, freezing the droplets by contact with a liquid freezant, recovering the frozen droplets, and lyophilizing them to remove water or other solvents.

BACKGROUND OF THE INVENTION

In the practice of such processes liquid feedstocks have been disintegrated into discrete droplets by one of two techniques. The first technique entails injecting the feedstock below the freezant surface. In this technique, the injection orifice is normally immersed in the freezant. See, for example, U.S. Pat. No. 3,484,946. This technology suffers from the disadvantage that a carefully heated injection orifice is required to prevent freezing of liquid in the immersed orifice with resultant plugging of the orifice by frozen feedstock. An attendant disadvantage is that once started the process cannot be conveniently stopped or interrupted: When the flow of liquid through the orifice stops, the residual liquid in the orifice will freeze at once. Thus this frozen material must be removed from the orifice before operations can resume. The heated orifice may also denature labile constituents in the liquid product. Finally, an undesirable proportion of fine product particles can result from the violent boiling of freezant at the interface between the heated orifice and the freezant.

The second and most widely adopted technique is denominated herein by the term "spray freezing." Typical spray freezing processes are exemplified in U.S. Pat. Nos. 3,228,838, 3,721,725, 3,928,566 and 3,932,943. In these processes, the liquid feedstock is atomized or formed into droplets prior to entering the freezant. However, we have found this method to be unsatisfactory where future uses or further processing of the lyophilized particles requires a low proportion of fine particles.

This is particularly the case with lyophilized biological fluids to be used as controls, standards or calibrators for various analytical or diagnostic test procedures, or for the instruments used to perform such test procedures. These products as a group will hereinafter be referred to as "quality control materials" and, where such materials are derived from a blood fraction, they are henceforth defined as "quanlity control plasma." Quality control plasma is intended to include serum, plasma, as well as defibrinated plasma. Aside from the problem of aerosol formation of potentially infective fluids, quality control materials prepared by spray freezing suffer from at least three deficiencies. These deficiencies are largely a function of the high proportion of fine particles in the lyophilized product. The term "fine particles" is used hereinafter to mean those particles which are capable of passing through United States Standard Mesh No. 20 as that mesh is ordinarily used to determine particle size. Stated differently, these are particles which have at least one cross-sectional dimension smaller than about 850 microns.

The first deficiency experienced with spray frozen product is that the fine particles acquire a static charge, particularly under the conditions of low humidity in which lyophilized substances are stored. The particles tend to adhere to one another and to the walls of their containers, thus making handling quite difficult. This difficulty in handling becomes especially significant during production of quality control materials.

If spray frozen, lyophilized biological fluids are to be employed as quality control materials they must be precisely weighed out into containers such as 10, 25 or 50 ml. vials, a process that will hereinafter be referred to as a "weigh and fill operation." One suitable device for accomplishing such weigh and fill operations is disclosed in U.S. Pat. No. 2,701,703. Other such devices are well known to those skilled in the art. The ordinary difficulty of rapidly and precisely weighing very small masses into containers with automatic equipment is exacerbated by electrostatically charged product, and fine particles create the most difficulty. The charged fine particles, because of their low mass, cling to the surfaces of the equipment and to one another or larger particles. This impedes the free flow of the material and continuously varies the container fill rates, often bringing containers over their weight tolerance limits. These limits are quite narrow in the case of quality control materials: If variable amounts of the lyophilized control are weighed into vials of the same lot, reconstitution in constant amounts of aqueous solution will yield a constituent variation that is directly proportional to the variation in control material from vial to vial. This is particularly undesirable with reconstituted standards.

Standards are generally biological fluids containing stated constituent concentrations. They are assayed by the laboratory using its reagents and instruments, and the results plotted against the manufacturer's stated concentrations of the assayed constituent. This plot is then used for a predetermined period to arrive at constituent levels for all samples tested. If this plot is in error because the actual constituent levels are different from the manufacturer's reported concentrations, the reported results for every patient sample compared with the plot would be in error as well.

Other liquid feedstocks which are to be formed into particles, lyophilized and weighed into containers are equally susceptible to severe quality control problems. For example, pharmaceutical dosages and diagnostic reagents require tolerances equally close to those of quality control materials. Here again, a large proportion of fine product particles makes it extremely difficult to achieve rapid, uniform, automated dispensing of product by weight.

The deficiencies of spray frozen liquid feedstocks do not end with variable container fills and concomitant high container rejection rates. Even if a container is filled with a mass of quality control material within the established weight tolerance it may nonetheless be completely unsatisfactory. This raises the second deficiency of quality control materials prepared by conventional spray freezing techniques: The concentrations of clinically significant constituents are not uniform over the entire range of particle sizes. For example, fine particles of human control serum may contain up to 10% less creatine phosphokinase activity than does the lyophilized material as a whole. Thus even if a container is filled to the proper weight it may contain a greater proportion of one particle size than other containers in the same lot of feedstock. Fine particles, for example, may predominate during the later portion of a filling operation. In such case the last vials of any control serum lot will exhibit artificially low creatine phosphokinase activity. Variation in constituent levels is as deleterious as variable fill levels, yet it is completely impractical to detect and reject such defective containers by individually assaying all of the containers in the lot.

The third deficiency of spray freezing stems from the required removal and disposal of excessive fine particles from the spray frozen compositions. Removing such particles from spray frozen quality control materials, for example by sieving, increases the electrostatic charge on the remaining fine particles. Sieving also alters constituent concentration in the final product as compared to the starting material because, as discussed above, constituent levels are not constant over the entire range of particle sizes. Finally, the fine particles removed from the spray frozen product are either waste or must be recycled through the process again, thereby at least doubling the processing costs for that proportion of product.

While it would be desirable to reduce the production of fine particles ab initio, it is equally important to avoid the formation of "large particles," i.e., those capable of being retained by United States Standard Mesh No. 12 at that mesh is ordinarily used to determine particle size. Stated differently, these large particles have at least one cross-sectional dimension larger than about 1650 microns. The disadvantage of large particles is that they tend to fracture, thus generating more unwanted fine particles as well as jagged fragments which impede the free flow of the particle mass.

It is therefore an object of this invention to produce a lyophilized product which can be accurately, rapidly and conveniently weighed from bulk lots into a plurality of uniform portions.

It is an additional object of this invention to provide a process and apparatus for freezing particles of a liquid feedstock wherein the flow of feedstock can be interrupted without additional processing disruptions, without high capital requirements or complex equipment, and without risking the destruction of labile constituents of the product.

It is another object of this invention to produce a frozen particulate composition in which the proportion of fine particles is significantly reduced without concomitantly increasing the proportion of large particles.

It is a further object of this invention to provide a process and apparatus for freezing particles of biological fluid which, when lyophilized, can be accurately and rapidly distributed by automatic weigh and fill devices from bulk lots into a plurality of uniform portions.

It is a still further object of this invention to produce a quality control material which is substantially homogeneous with respect to the concentrations of its constituents and which can be employed in weigh and fill systems without resulting in excessive rejection rates of filled containers for overfilling.

These and other objects of this invention will be apparent to those skilled in the art from a consideration of this specification taken in its entirety.

SUMMARY OF THE INVENTION

The above objectives are accomplished by forming the liquid feedstock into a continuous stream of liquid, preferably by passing the feedstock through an orifice, and then bringing the continuous stream of liquid into contact with a liquid freezant without contact between the liquid freezant and the means used to form the continuous stream of liquid feedstock. Generally, this will entail passing a continuous liquid stream of the feedstock through a gaseous zone and into or onto the freezant liquid. We have surprisingly discovered that the particles of frozen liquid feedstock obtained by employing a continuous stream of liquid rather than a spray of liquid exhibit remarkably low levels of fine particles without a simultaneous increase in the proportion of large particles. This particle size homogeneity is retained after lyophilization of the frozen particles. It facilitates filling containers with constant, reproducible quantities of lyophilized product and it reduces the likelihood of serum constituent maldistribution.

The lyophilized particulate composition obtained by the method of this invention illustratively contains about 66.5 to 92% by weight of particles in the desired size range of 12–20 mesh, up to 6% by weight unwanted large particles in the size range larger than 12 mesh, and about 7 to 33.5% by weight unwanted fine particles in the size range smaller than 20 mesh. Preferably, the lyophilized particulate compositions of this invention contain about 75 to 100% by weight of particles in the 12–20 mesh range and 0 to 25% by weight of particles in a size range other than 12–20 mesh. The most preferred lyophilized particulate compositions of the invention contain about 87 to 92% by weight of 12–20 mesh particles, about 1 to 6% by weight of particles larger than 12 mesh and about 7 to 11% by weight of particles smaller than 20 mesh.

The above lyophilized particle sizes are those obtained prior to any sieving whatsoever. While sieving is unnecessary in view of the reduction in fine particles achieved by use of the continuous stream, the lyophilized product prepared by the process of this invention may, of course, be sieved to even further enhance the reduction in fine and large particules. For example, a lot of quality control material can be first passed through 12 mesh to retain large particles. A proportion of fine particles is then removed by sieving the product on 20 or 30 mesh. The disadvantages associated with sieving which are discussed above are substantially reduced, however, where the starting level of fine particles is so substantially diminished.

DESCRIPTION OF THE PREFERRED EMBODIMENTS

Figure 1:
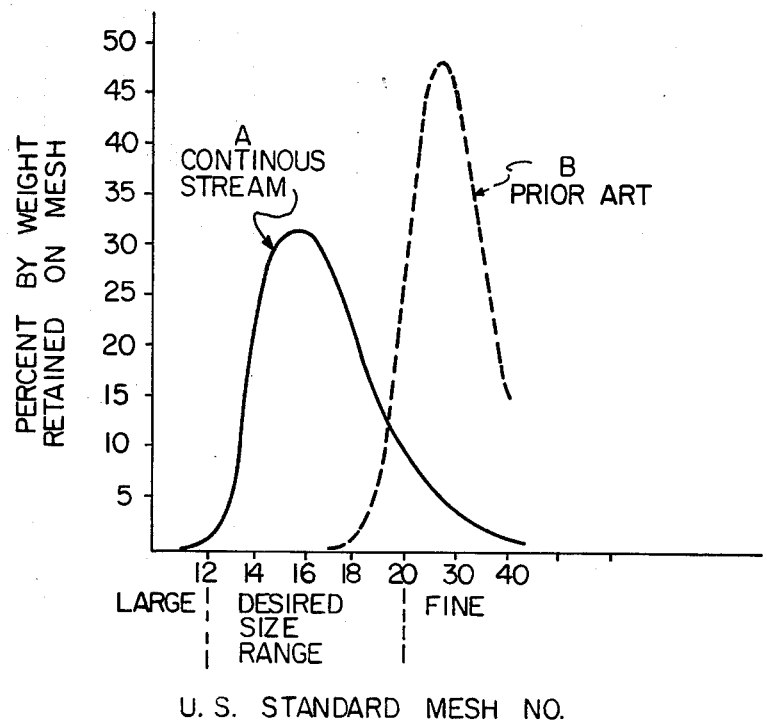
FIG. 1 presents a comparison of the averaged particle size distribution data from (1) three lots of lyophilized human quality control plasma prepared by the prior art process of spray freezing (Graph B) and (2) three lots of the human quality control plasma prepared by the continuous stream process of this invention (Graph A). The data in Graph A represents a preferred embodiment of the invention and demonstrates that the continuous stream technique produces a lyophilized product most of whose particles are in the desired 12–20 mesh range whereas most of the particles of the prior art spray-frozen product are in the undesirable fine particle range of less than 20 mesh.

Any liquid material capable of being chilled while remaining in liquid form to a temperature sufficiently low to freeze the feedstock in question can be utilized as the liquid freezant. The liquid freezant is generally immiscible with the selected liquid feedstock, preferably inert with respect to the product constituents, readily removable from the frozen liquid product without depositing a contaminating residue, and preferably of higher density than the frozen liquid feedstock so that the feedstock can be recovered from the freezant surface. Preferred freezants exhibiting these characteristics are halocarbons such as fluorine and chlorine derivatives of hydrocarbons containing up to 5 carbon atoms. An especially preferred freezant is dichlorodifluoromethane, sold under the trade name "Freon 12" by E. I. du Pont de Nemour and Company, Inc. Other liquid freezants which may be used in the process of this invention include liquid nitrogen, liquid air, hydrocarbons such as heptane, and mixtures of freezants such as heptane and trichlorotrifluoromethane. Other suitable freezants will readily be apparent to those skilled in the art.

The temperature of the liquid freezant is preferably maintained at or near its boiling point. If the freezant is permitted to boil the resulting ebullition agitates the freezant, thereby reducing the tendency of the liquid product droplets to agglomerate before they can be frozen. Further, the boiling freezant should also be in motion relative to the continuous stream of liquid feedstock being introduced. Preferably, it is circulated in an orderly, unidirectional fashion to remove frozen particles from potential contact with incoming liquid feedstock and to facilitate collection of the frozen particles. A rate of movement of freezant of from about 2.5 ft./sec. to about 8 ft./sec. relative to the introduced feedstock yields satisfactory results. A rate of about 4.7 ft./sec. is preferred.

While the rate of movement of the freezant will affect particle size distribution, the predominant feature of the present process is that the liquid feedstock enter the freezant in a continuous stream without any contact between the freezant and the orifice or other means by which the continuous stream of liquid feedstock is formed. A change in orifice size, in the distance from the orifice to the freezant, or in the pressure or the solids content of the feedstock will not significantly reduce the proportion of fine particle sizes unless a continuous liquid feedstock stream is achieved. In the practice of this invention each of these four parameters may be adjusted over a considerable range so long as the remaining factors are established or adjusted to ensure a continuous, substantially integral or intact feedstock stream.

Feedstock solids content is generally increased by boosting protein concentration. For example, human blood plasma contains approximately 6 gram percent of protein, but this concentration can be readily increased to 12 gram percent or more by conventional ultrafiltration techniques. This concentrated plasma is then treated in accordance with the process of this invention. However, if the solids content of feedstock is increased, for example, maintenance of a continuous feedstock stream may require a reduction in the distance from the orifice to freezant and an increase in both the orifice size and feedstock pressure. Generally, a solids content of from about 4 gram percent to about 30 gram percent is satisfactory while a solids content of about 11 gram percent is preferred.

The pressure applied to the feedstock is a second factor to be considered in establishing and maintaining a continuous feedstock stream. Under ordinary circumstances a pressure range of from about 3 psig to about 15 psig is acceptable. The preferred pressure is 7 psig. If the pressure is too low a large proportion of large particles is formed. If it is too high an unacceptable proportion of fine particles is produced. Again, if the pressure is changed it may be necessary to change one or more of the remaining parameters of feedstock solids content, orifice diameter and distance from orifice to freezant. For example, a decrease in pressure may necessitate a reduction in both the orifice diameter and the distance from orifice to freezant.

A third factor to be considered is the distance through which the feedstock passes before it contacts the freezant, e.g., the gaseous space separating the feedstock orifice or other continuous stream-forming device from the freezant surface. If this distance is excessive, the feedstock viscosity, the orifice diameter and the pressure on the feedstock may be unable to adequately compensate with the result that the stream will fragment into spray before it enters the freezant. A distance which generally will a continuous stream of liquid feedstock ranges from a span just sufficient to protect the feedstock from freezing in the orifice, ordinarily 1 cm., up to 5 cm. The optimal distance with human blood plasma feedstock is from about 1 cm. to about 3 cm., with about 2 cm. being preferred.

A fourth factor is orifice size and configuration. The orifice is ordinarily circular, free of burrs or other irregularities and has an outlet which is parallel to the freezant surface. The opening diameter generally ranges from about 540/10,000 inch to about 95/10,000 inch. A range of from about 155/10,000 to about 195/10,000 inch is preferred. For example, blunt end needles between 15 and 26 ga. may be employed, but 21 or 22 ga. needles have been used with most favorable effect. The smaller the opening the more likely the stream is to form a spray. If for example the orifice opening is reduced it may be necessary to increase the feedstock solids content, reduce the separation of orifice and freezant surface or reduce the feedstock pressure.

The continuous stream of feedstock is preferably a substantially uniform, non-fragmented cylinder of liquid extending perpendicularly to the freezant surface. However, the stream may also be irregular in shape, appearing as a dribble or fan of fluid. It may enter the freezant at an angle to the freezant surface and it may oscillate. Further, the stream may be relatively short lived, e.g., it may be supplied in pulses, provided, of course, that it does not take on the configuration of a spray or a plurality of droplets. All that is required is for a substantially unbroken stream of liquid feedstock to come into contact with the freezant.

A wide variety of liquid feedstocks can be employed in the process of this invention. Biologically active substances such as pharmaceuticals, proteins including antigens, antibodies and enzymes, organisms including bacteria and viruses, and body fluids may be employed as solutions or slurries in water or other solvents. The feedstock may be purified or contaminated, depending upon the desired end use. The preferred feedstock for purposes of this invention is a human blood component such as serum or plasma. The blood component may be used without further processing or it may contain added reagents such as enzymes or inorganic salts.

The lyophilized products of this invention, particularly blood components such as serum, may be readily combined from a plurality of production lots into a single master lot. While production lots can be combined in liquid form before lyophilization, this is not preferred. Production lots typically contain from about 500 to about 2500 liters where the lots are quality control materials manufactured from human blood serum. This volume when distributed into vials is the maximum range that can be accommodated in generally available commercial lyophilizers. Such lots are ordinarily discrete pools of defibrinated plasma made by the accumulation of plasma samples from a large number of donors. These lots or pools will of course each contain different constituent levels and, when lyophilized, may even contain variations among different vials in the same lot. For example, while the moisture content is often substantially the same from vial-to-vail in some cases, it may vary from one lyophilization batch to another. This vial-to-vial and lot-to-lot constituent variation may be eliminated for commercial scale quantities of product by dry blending the lyophilized production lots into a single master lot of homogeneous composition. The manufacture of such master lots is greatly facilitated by the improved characteristics of the products of this invention. It is neither necessary, for example, to vacuum dry or otherwise process the product after lyophilization nor to redissolve the production lots before combining the lots to form a master lot. In fact, passing quality control materials through multiple cycles of reconstitution and lyophilization is deleterious to labile substances such as enzymes. This uniform dry blending of production lots is facilitated by the relatively high distribution of properly sized particles (12-20 mesh) in each of the lots. Thus the master lots of this invention can be dry-weighed into vials with the assurance that there will be substantially no vial-to-vial variation in product quality or constituents because of variations among or within production lots. This allows the user to rely with confidence on the product constituent assays furnished by the manufacture and reduces the amount of constituent assaying by the manufacturer.

A suitable apparatus for the practice of this invention comprises a vessel for holding a liquid freezant at a predetermined level, a liquid feedstock introduction system or injection means through which said feedstock is passed, pressurizing means for expelling said feedstock through said injection means and a mounting means for fixing said injection means at a predetermined distance from the level of said freezant. The dimensions of the orifice, the pressure supplied by said pressurizing means and the predetermined distance fixed by said mounting means are all selected so that the feedstock will enter the freezant as a continuous, intact stream.

Figure 2:
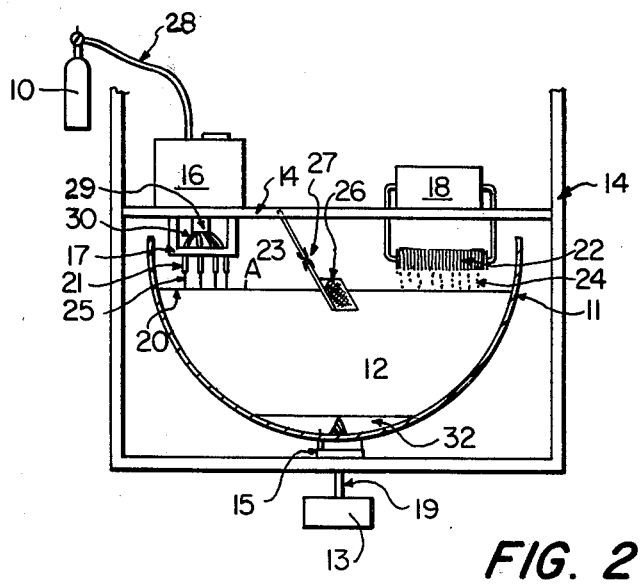
FIG. 2 is a schematic drawing showing a preferred embodiment of an apparatus for carrying out the continuous stream freezing process of this invention.

A preferred apparatus is shown in FIG. 2. A frame 14 supports vessel 11 and associated bearings 15, feedstock reservoir 16, nozzle mount 17, clamp 27 and compressor 18. The vessel 11 is rotatable by shaft 19 driven by motor 13. Vessel 11 is hemispherical in shape and can be constructed of any material, for example, aluminum alloy or stainless steel, which is suitable for use with low temperature freezant 12. Feedstock reservoir 16 communicates by pressure line 28 to a conventional source of pressure such as a tank of compressed gas 10. The flow of feedstock from reservoir 16 is controlled by valve 29 in fluid communication with distribution lines 30 and nozzles 21. Frame 14 also supports both wire mesh scoop 26, by way of its attendant clamp 27, and heat exchanger 22 powered by compressor 18.

In use, vessel 11 is filled with freezant 12 to level 20. Level 20 is a predetermined distance A from the end of nozzles 21. Vessel 11 is then rotated about its axis on shaft 19 to induce rotation of freezant 12. The baffles 32 in the bottom of the vessel 11 enhance the circulation of freezant 12. The freezant is allowed to boil (most suitable freezants will boil at room temperature) but the vapors are condensed by heat exchanger 22 in gaseous zone 23 and the condensate 24 is allowed to drip back into freezant 12. Feedstock reservoir 16 is pressurized through line 28 by a canister of gaseous nitrogen 10. Valve 29 is opened and the feedstock then allowed to pass from nozzles 21 in a continuous, substantially cylindrical stream 25 through the gaseous zone 23 and into freezant 12. The frozen particles, which are formed immediately, are collected for removal in screen wire scoop 26. The scoop 26 may then be detached from frame 14 by disengaging clamp 27. Scoop 26 may be advantageously located at the freezant surface where the feedstock is human blood plasma and the freezant is dichlorodifluoromethane because the frozen plasma particles will float on the dichlorodifluoromethane.

The frozen particles recovered from vessel 11 are then lyophilized using conventional lyophilization techniques and equipment well known to those skilled in the art. The lyophilized particles are then dry-weighed into vials or other suitable containers. The vials are then hermetically sealed to complete manufacture. Alernatively, two or more separate lots of lyophilized particles can be dry-blended, for example in a tumble blender, until a uniform master lot is prepared. The vials are then dry-filled from the master lot and hermetically sealed.

The following examples are intended to further illustrate the invention although it will be understood that the invention is not limited to these specific examples.

EXAMPLE I

This Example demonstrates the substantial reduction in fine particles obtained by passing a continuous stream of defibrinated human blood plasma into the freezant as compared to the results obtained with a discontinuous stream or spray. The apparatus of FIG. 2 having a vessel diameter of 30 inches was filled with dichlorodifluoromethane as "Freon 12" at $-30°$ C. and the vessel rotated at about 35 rpm to produce an average freezant surface speed of 7.85 ft./sec. at the points of plasma introduction. The plasma solids content was 6.5 gram percent, the nozzle was a 23 ga. needle, and $7.5\pm0.25$ psig $N_2$ pressure was applied to the plasma. The plasma temperature was $4°\pm1°$ C. The comparison between continuous and discontinuous streams was then made by moving the nozzle orifice incrementally closer to the freezant surface until a continuous stream entered the freezant. When the distance between the nozzles and the freezant surface was greater than 2 cm., a spray of blood plasma was invariably produced prior to its contacting the freezant. On the contrary, at distances of 2 cm. or less, the plasma was a continuous, intact, cylindrical stream at the point it first made contact with the freezant. Distances as short as 0.5 cm. were studied. The frozen particles were separately collected from the runs conducted at each distance, lyophilized and sieved through successively smaller U.S. Standard Mesh employing an ATM Sonic Sifter model L3P according to the instructions provided therewith. The distribution of particles is expressed as the percentage of total particle weight collected rounded off to the nearest tenth of a percent. the particle size range is equivalent to the mesh openings as recited on the U.S. Standard Sieves provided with the above device.

PARTICLE DISTRIBUTION AS A FUNCTION OF THE
DISTANCE FROM ORIFICE TO FREEZANT SURFACE

| Particle Size Range (Microns) | Mesh Size | Distance from Orifice to Freezant Surface | | | |
|---|---|---|---|---|---|
| | | 40 cm. | 20 cm. | 5 cm. | 0.5–2 cm. |
| >1650 | >12 | 0 | 0 | 0 | 0.9 |
| 1650–1400 | 12–14 | 0 | 0 | 0 | 5.0 |
| 1400–1180 | 14–16 | 0.2 | 0 | 0 | 9.7 |
| 1180–1000 | 16–18 | 3.5 | 2.3 | 3.0 | 24.0 |
| 1000–850 | 18–20 | 17.6 | 19.4 | 21.0 | 27.7 |
| 850–600 | 20–30 | 49.6 | 39.7 | 49.6 | 17.9 |
| 600–425 | 30–40 | 15.0 | 24.3 | 12.6 | 4.8 |
| <425 | <40 | 14.0 | 14.3 | 13.8 | 9.9 |

The transition from spray to continuous stream substantially modified the particle size distribution. Particularly noteworthy is the predominance of 12 to 20 mesh particles obtained at distances of 0.5–2 cm. (continuous stream distances) which applicant has found to be especially desirable for use in automated weigh and fill devices. These particles constituted an average of only 22.3% of the total when the plasma entered the freezant as a spray but rose to 66.5% when the plasma entered as a continuous stream. Thus, by establishing a continuous stream, three times as much product in the particularly desirable 12 to 20 mesh range was obtained. This clearly establishes the advantage of introducing the feedstock into the freezant as a continuous intact stream.

EXAMPLE II

The parameters of Example I were modified to further enhance the production of 12 to 20 mesh particles and three different lots of human blood plasma were processed to determine the reproducibility of continuous stream freezing. The process of Example I was followed except that a 22 ga. needle was employed, the plasma pressure was maintained at 7.0±0.25 psig N$_2$, the plasma had been concentrated by ultrafiltration to about 11 gram percent protein prior to its introduction into the freezant, and the distance from the needle orifice to the freezant surface was increased to 3.0 cm. A continuous cylindrical, intact stream of plasma impacted the freezant surface in all runs of this Example. A total of 8.8 to 9.1 liters of plasma from each lot was treated in each run. The results tabulated below are expressed as percentages, by weight of the total lyophilized product collected rounded off to the nearest whole integer.

| Particle Size Range (Microns) | Mesh Size | Serum Lot | | |
|---|---|---|---|---|
| | | A | B | C |
| >1650 | >12 | 6 | 2 | 1 |
| 1400–1650 | 12–14 | 28 | 19 | 23 |
| 1180–1400 | 14–16 | 26 | 32 | 32 |
| 1000–1180 | 16–18 | 20 | 23 | 23 |
| 850–1000 | 18–20 | 13 | 16 | 14 |
| 600–850 | 20–30 | 5 | 7 | 5 |
| <600 | <30 | 2 | 4 | 2 |

The results for lot C are plotted in FIG. 1 as Curve A. The average of the three runs reported in Example 1 for the prior art spray freezing process (40 cm., 20 cm. and 5 cm.) are plotted in FIG. 1 as Curve B. Comparison of these two curves shows at once the tremendous predominance of unwanted fine particles produced by the prior art process in comparison with the low proportion obtained by the continuous stream process of this invention. This comparison also shows the very high proportion of desirable 12–20 mesh particles obtained by the process of this invention as compared to that obtained using the freeze spraying process of the prior art.

The above examples and other specific information contained herein are for purposes of illustration only, and such alterations and modifications thereof as would be apparent to those skilled in the art are deemed to fall within the scope and spirit of the invention, bearing in mind that the invention is defined only by the claims appended hereto.

What is claimed is:

1. A method for producing dry particles, of which about 1 to 6% by weight are larger than 12 Mesh, from a liquid feedstock containing water and a biologically active substance selected from the group of antibodies, pharmaceuticals, bacteria, viruses and human body fluids, comprising providing a bath of liquid freezant at a temperature 0° C. in communication with a gaseous zone, passing a continuous stream of said feedstock through said zone and into an orderly, unidirectional flow of said freezant, recovering frozen pellets of said feedstock and lyophilizing said pellets.

2. The method of claim 1 wherein the continuous stream has the configuration of a substantially uniform cylinder.

3. The method of claim 1 wherein the substance is a pharmaceutical.

4. The method of claim 1 wherein the feedstock contains from about 4 gram percent to about 30 gram percent of solids with the remainder being water.

5. A method for producing a quality control material, comprising passing a continuous stream of said material through a gaseous zone and into a freezant liquid to form frozen particles of said material, recovering said lyophilizing the particles, filling a predetermined mass of the particles into a container and hermetically sealing said container.

6. A method for producing frozen particles of quality control material from a human blood component having a solids content of about 4 gram percent to about 30 gram percent, which comprises forming said component into a substantially continuous stream by passing it through an about 540/10,000 to about 95/10,000 inch orifice at a pressure of about 3 psig to about 15 psig, directing said stream through a gaseous zone disposed between said orifice and a moving surface of a boiling halocarbon freezant moving at a rate relative to said stream of about 2.5 to about 8 feet per second and into the surface of said freezant, the distance between said orifice and said surface of freezant being about 1 to about 5 centimeters, whereby said component enters said freezant and is frozen into particles at least about 75% by weight of which are, after lyophilization, in the 12 to 20 mesh size range.

7. The method of claim 6 wherein the pressure is about 7 psig, the freezant surface moves at about 4.7 ft./sec., the distance between said orifice and said freezant surface is about 2 cm., the solids content of said component is about 11 gram percent, and said orifice is about 195/10,000 inch.

8. The method of claim 7 wherein at least about 87% by weight of said lyophilized particles are in the 12–20 mesh size range.

9. A method for improving the lot size and lot uniformity of a lyophilized biologically active substance which comprises the steps of (1) preparing a first lot of said substance by (a) passing said substance into a moving liquid freezant to thereby form frozen particles of said substance; and
(b) lyophilizing said frozen particles to produce lyophilized particles;

(2) preparing one or more additional lots of said substance in the same manner as said first lot was prepared;

(3) mixing the lyophilized particles of said first lot and said one or more additional lots;

(4) dispensing the blend of lots produced in step (3) above into suitable containers; and (5) sealing said containers.

10. The method of claim 9 wherein the lots are not vacuum dried after lyophilization.

11. The method of claim 9 wherein the lyophilized particles are not reconstituted before being mixed.

12. The method of claim 9 wherein the lots have substantially the same moisture content.

13. The method of claim 9 wherein about 75 to 100% by weight of the particles in (a) said first lot, (b) said one or more additional lots, or (c) the lot produced by mixing (a) and (b) are in the 12-20 mesh size range and the rest are in a size range other than 12-20 mesh.

14. The method of claim 9 wherein about 87 to 100% by weight of said particles are in the 12-20 mesh size range.

15. The method of claim 9 wherein the substance is defibrinated plasma.

16. A method for producing a sealed container of lyophilized feedstock particles, comprising concentrating the solids in said feedstock, passing said concentrated feedstock in a continuous stream through a gaseous zone and into a freezant liquid, recovering said particles of feedstock from said freezant liquid, lyophilizing said particles, filling a container with the lyophilized particles, and hermetically sealing said container.

17. The method of claim 16 wherein the solids are concentrated by ultrafiltration.

18. The method of claim 16 wherein the solids concentrated are proteins.

19. The method of claim 18 wherein the protein is concentrated to about 12 gram percent.

20. The method of claim 16 wherein the feedstock is a biologically active substance.

21. A method for producing a sealed container of lyophilized particulate control material from human blood plasma, comprising concentrating the protein in said plasma, passing said concentrated plasma in a continuous stream through a gaseous zone and into a freezant liquid, recovering frozen plasma particles from said freezant liquid, lyophilizing said particles, filling a container with the lyophilized particles, and hermetically sealing said container.

22. The method of claim 21 wherein two or more lots of said lyophilized plasma particles are mixed and the containers are filled with the resulting mixture of lots.

23. The method of claim 21 including the additional step of assaying at least one constituent of said control material.

24. In a method for producing frozen particles of blood plasma or serum wherein said plasma or serum is passed through an orifice and into a liquid freezant at a temperature below the freezing point of said plasma or serum without said orifice contacting said freezant, the improvement comprising passing a continuous stream of said plasma or serum into said freezant.

25. A method which comprises passing a continuous stream of a blood component solution through a gaseous zone and into a freezant liquid at a temperature below the freezing point of said component whereby frozen pellets of said blood component solution are formed.

* * * * *

UNITED STATES PATENT AND TRADEMARK OFFICE
CERTIFICATE OF CORRECTION

PATENT NO. : 4,211,015
DATED : Jul. 8, 1980
INVENTOR(S) : Thomas H. Adams, James P. Beck and Robert C. Menson It is certified that error appears in the above-identified patent and that said Letters Patent are hereby corrected as shown below:

In title, delete "AND APPARATUS".

Column 1, line 53, "quanlity" should be --quality--.

Column 3, line 24, "at" should be --as--.

Column 4, line 36, "particules" should be --particles--.

Column 7, line 36, "manufacture" should be --manufacturer--.

Signed and Sealed this

Fourteenth Day of October 1980

[SEAL]

Attest:

Attesting Officer

SIDNEY A. DIAMOND

Commissioner of Patents and Trademarks